US00PP33598P3

(12) United States Plant Patent
MacGregor et al.

(10) Patent No.: US PP33,598 P3
(45) Date of Patent: Nov. 2, 2021

(54) ***GEUM* PLANT NAMED 'MACGEU005'**

(50) Latin Name: ***Geum* hybrid**
Varietal Denomination: MACGEU005

(71) Applicants: Alasdair MacGregor, Kirkcudbright (GB); Elizabeth MacGregor, Kirkcudbright (GB)

(72) Inventors: Alasdair MacGregor, Kirkcudbright (GB); Elizabeth MacGregor, Kirkcudbright (GB)

( * ) Notice: Subject to any disclaimer, the term of this patent is extended or adjusted under 35 U.S.C. 154(b) by 0 days.

(21) Appl. No.: 16/906,282

(22) Filed: Jun. 19, 2020

(65) Prior Publication Data

US 2021/0127539 P1 Apr. 29, 2021

(51) Int. Cl.
*A01H 5/02* (2018.01)
*A01H 6/74* (2018.01)
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
CPC ..... A01H 5/02; A01H 5/00; A01H 6/74
See application file for complete search history.

(56) References Cited

PUBLICATIONS

Floral Daily 2019 UK: Award winning new plant display from Farplants, retrieved on Nov. 19, 2020, retrieved from the Internet at https://www.floraldaily.com/article/9120355/uk-award-winning-new-plant-display-from-farplants/, 6 pp. (Year: 2019).*
Prenplants Sussex Limited 2019 Peat Free Plants Catalogue, retrieved on Mar. 10, 2021, retrieved from the Internet at http://www.prenplants.co.uk/wp-content/uploads/2018/12/Prenplants-Catalogue-2019.pdf, intro page, pp. 1 and 26. (Year: 2018).*

* cited by examiner

*Primary Examiner* — June Hwu
(74) *Attorney, Agent, or Firm* — Samuel R. McCoy, Jr.

(57) ABSTRACT

'MACGEU005' is a new and distinctive variety of *Geum* plant which is characterized by large dark green leaves, an abundance of red-orange doubled flowers and a long bloom period. The new variety propagates successfully by stem cuttings and tissue culture and has shown to be uniform and stable in the resulting generations from asexual propagation.

3 Drawing Sheets

Latin name of the genus and species: The Latin name of the genus and species of the novel variety disclosed herein is *Geum* hybrid.

Variety denomination: The inventive variety of *Geum* hybrid disclosed herein has been given the variety denomination 'MACGEU005'.

CROSS REFERENCE TO RELATED APPLICATIONS

This application claims priority to the Community Plant Variety Rights application number 2019/2734, filed Oct. 28, 2019, which is herein incorporated by reference.

BACKGROUND OF THE INVENTION

Parentage: 'MACGEU005' is the result of a controlled cross-pollination breeding program carried out by the inventors at their commercial nursery in Kirkcudbright, Scotland, in June of 2010. The inventors performed a controlled cross-pollination of the emasculated seed parent, *Geum* sp. 'Hannay's' (unpatented), with *Geum chiloense* 'Red Dragon' (unpatented), the pollen parent. Said pollination was performed in an insect proof environment. Seed from said cross was harvested, then germinated, and the resulting seedlings were then grown to a mature size in a protected poly tunnel greenhouse. In June of 2012, the inventors first observed the new *Geum* cultivar and noted it for its unique flower and bloom characteristics. Upon further observation to confirm the uniqueness and stability of the characteristics first observed, the new variety was selected for commercialization in June of 2014. This new and distinctive cultivar was given the name 'MACGEU005'.

Asexual Reproduction: Asexual reproduction of 'MACGEU005' was first accomplished in April of 2016 by way of vegetative division and subsequently by way of meristematic tissue culture micro propagation at a laboratory in Rijswijk, the Netherlands. Successive generations have shown that the unique features of the instant cultivar are stable and reproduce true to type.

SUMMARY OF THE INVENTION

The cultivar 'MACGEU005' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Geum* cultivar, 'MACGEU005'.

1. *Geum* 'MACGEU005' exhibits large, dark green leaves; and
2. *Geum* 'MACGEU005' exhibits an abundance of red-orange doubled flowers; and
3. *Geum* 'MACGEU005' exhibits a long bloom period.

BOTANICAL DESCRIPTION OF THE PLANT

Figure 1:
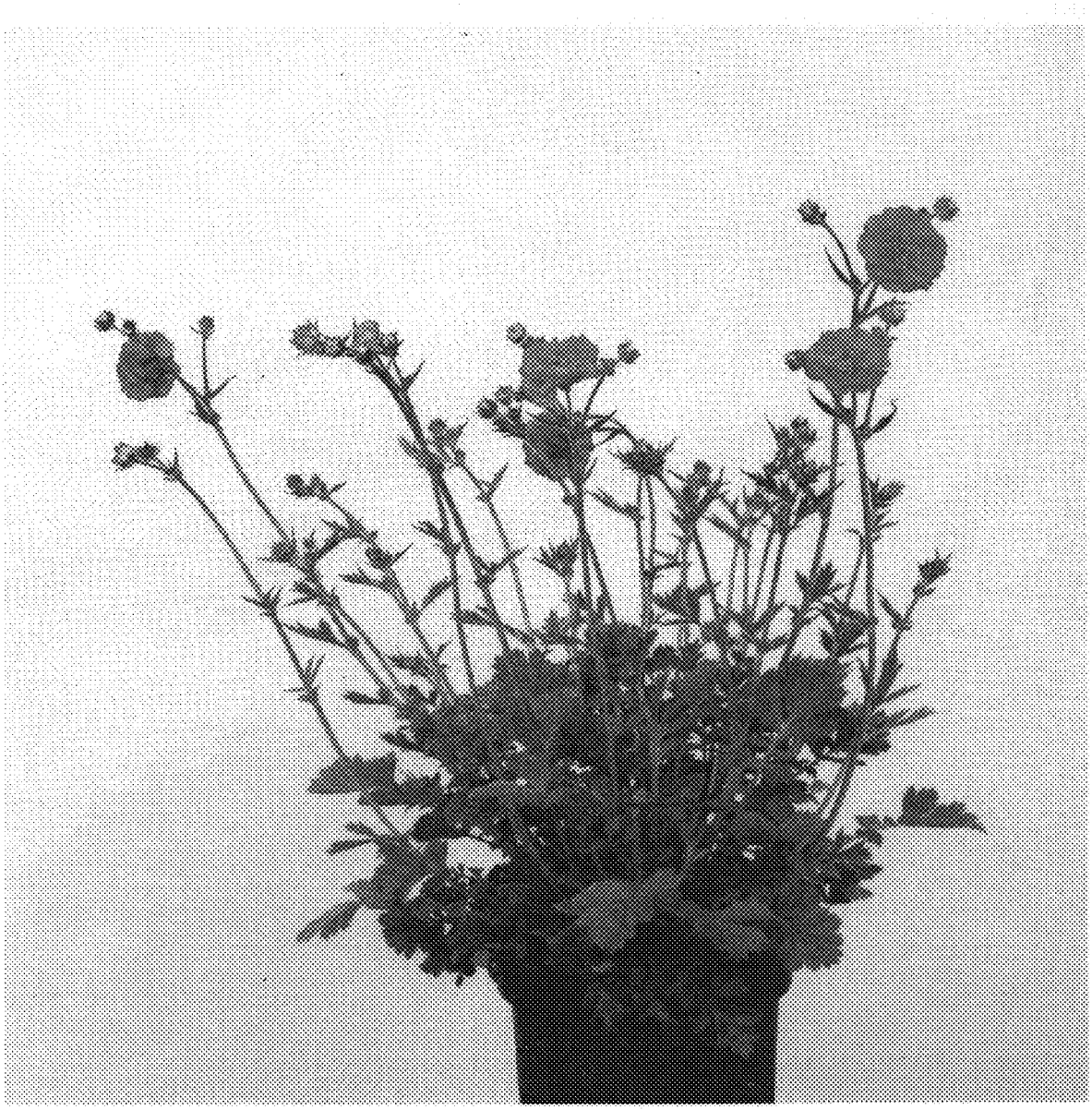
FIG. 1 shows, as nearly true as it is reasonably possible to make the same in color illustrations of this type, the typical foliage and growth characteristics of the new cultivar, 'MACGEU005'. The plant shown is approximately 4.5 month old, potted into a 3 liter nursery pot, grown outdoors in Kirkcudbright, Scotland at a commercial nursery.
Figure 2:
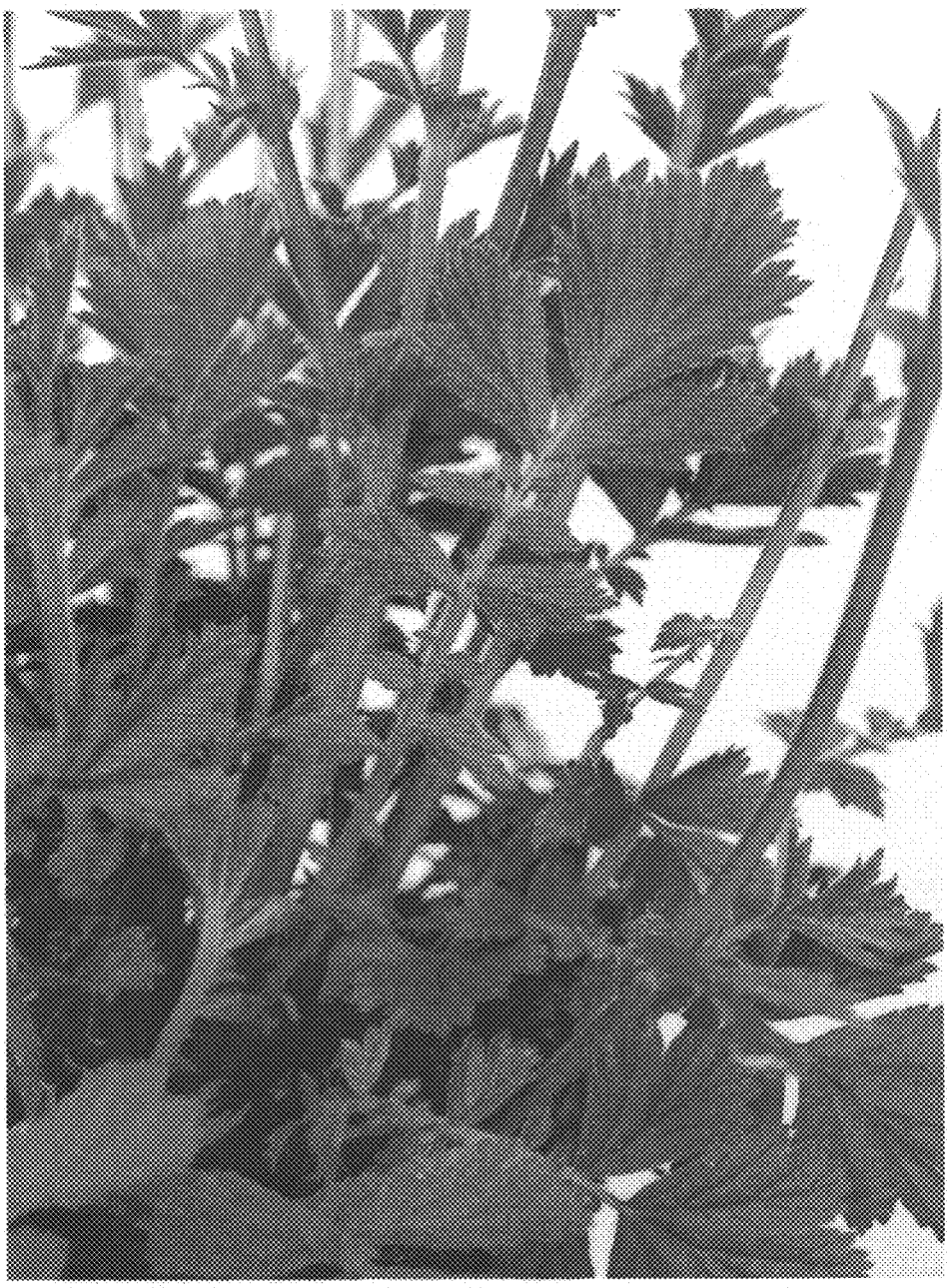
FIG. 2 shows, as nearly true as it is reasonably possible to make the same in color illustrations of this type, the typical foliage of the plant in FIG. 1.
Figure 3:
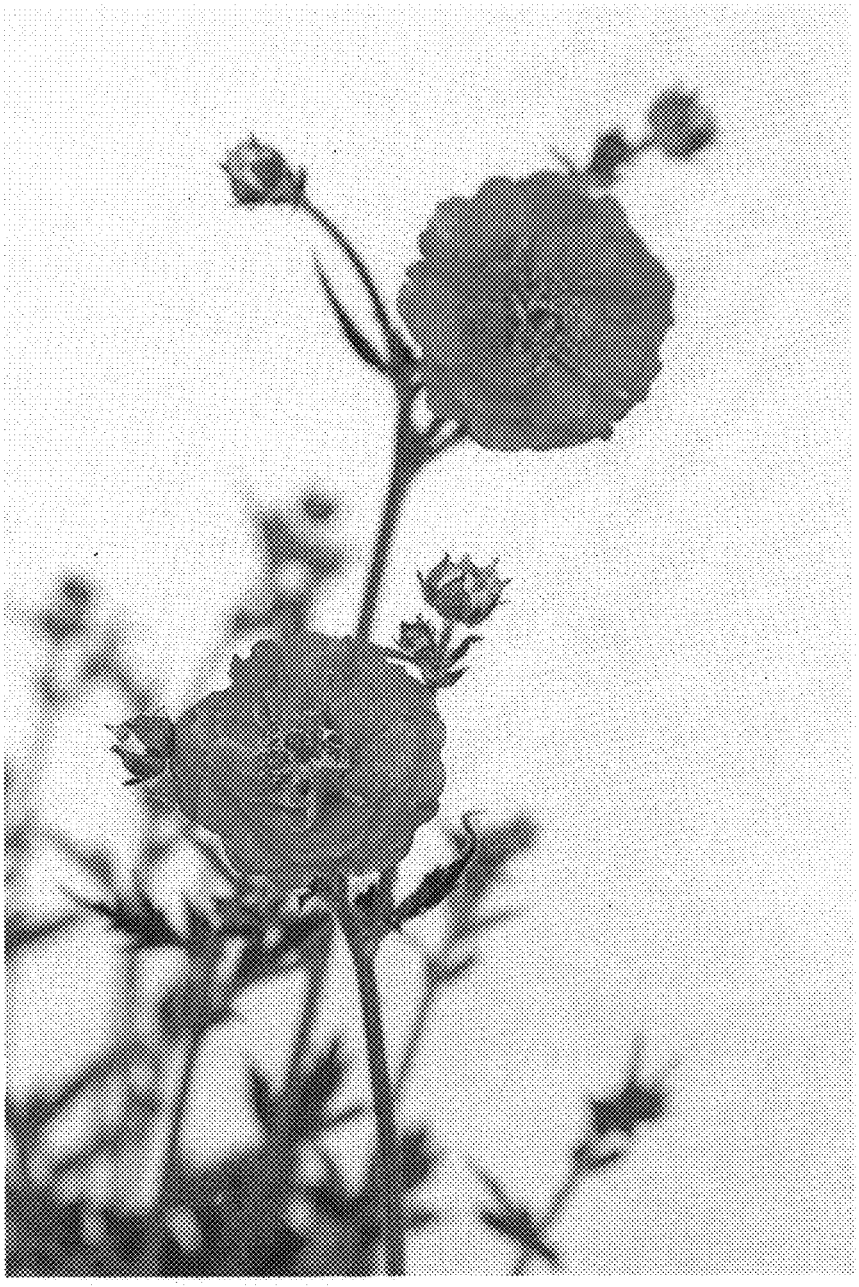
FIG. 3 shows, as nearly true as it is reasonably possible to make the same in color illustrations of this type, the typical flower of the plant in FIG. 1.

The following is a detailed botanical description of a new and distinct variety of *Geum* known as 'MACGEU005', based upon observations of 4.5 month old plants grown outdoors in Kirkcudbright, Scotland. Plants were grown with full sun to partial shade exposure and subsisted on natural rainfall with supplemental irrigation provided during periods of dry weather. Plants were grown in a nutrient-rich compost but were otherwise not given any supplemental fertilizer. No chemical pest treatments were given to the plants. Observation data was recorded in May of 2020.

Those skilled in the art will appreciate that certain characteristics will vary with older or, conversely, with younger plants. 'MACGEU005' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2007 edition.

A botanical description of 'MACGEU005' and comparisons with the parents and most similar variety of common knowledge are provided below.

General plant description:

*Growth habit*.—Herbaceous perennial with no lateral branching, flowering stems arising from the base, and inflorescence held above the foliar plane.

*Plant profile*.—Globular.

*Height*.—19.1 cm to the top of the foliar plane; 44.0 cm to the top of the floral plane.

*Spread*.—60.5 cm.

*Plant vigor*.—Moderately vigorous.

*Growth rate*.—Moderately fast growing.

*Propagation*.—Method — Meristematic tissue culture. Time to initiate rooting — 12 days at an average ambient temperature of 22 degrees Celsius. Time to produce flowering plant from rooted cutting — Approximately 4 months in a 15 cm container; 6 months in a 17 cm container.

*Pest resistance and susceptibility*.—Not any more or less susceptible to pests or diseases known to effect *Geum*.

*Environmental tolerances*.—Adapt to, at least, USDA Zones 5 to 9 and temperatures ranging from minus 25 degrees Celsius to 35 degrees Celsius; low to moderate tolerance to rain; moderate to high tolerance to wind.

Root system: Thin, fibrous, and freely branched.

Stem:

*Branching habit*.—Basally branched; moderately free branching.

*Number of primary (main) stems per plant*.—11.

*Number of secondary (lateral) branches per plant*.—None.

*Attitude*.—Average angle of 40 degrees from vertical; stems vary from between 0 to 80 degrees from vertical.

*Aspect*.—Rounded.

*Length*.—36.6 cm.

*Diameter*.—0.4 cm.

*Internode length*.—5.5 cm.

*Texture*.—Densely pubescent; hairs are soft, white RHS N155A, and 0.1 cm long, on average.

*Luster*.—Moderately glossy.

*Strength*.—Strong.

*Color, juvenile*.—Greyed-orange, nearest to RHS 166A.

*Color, mature*.—Yellow-green, nearest to RHS 144A, and suffused with greyed-orange when exposed to light, nearest the RHS 166A.

*Color at internodes*.—Yellow-green, nearest to RHS 144A.

Foliage:

*Arrangement*.—Leaves are borne both basally and on stems; on stems, arrangement is alternate.

*Basal leaves*.—Attachment — Petiolate. Division — Simple. Leaf shape — Lyrate. Dimensions — 20.9 cm long, including petiole, and 5.8 cm wide. Leaf attitude — Leaves in an average angle of 50 degrees to the stem. Leaf apex — Acute. Leaf base — Straight to truncate. Leaf margin — Biserrate. Texture, adaxial and abaxial surfaces — Smooth, pubescent. Pubescence, adaxial and abaxial surfaces — Soft, appressed to strigose hairs with an average length of 0.1 cm; colored a translucent white, nearest to RHS N155A. Luster, adaxial surface — Matte. Luster, abaxial surface — Matte. Color — Juvenile foliage color, adaxial surface — Green, nearest to RHS 143B. Juvenile foliage color, abaxial surface — Yellow-green, nearest to RHS 146C. Mature leaf color, adaxial surface — Green, nearest to RHS 137B. Mature leaf color, abaxial surface — Yellow-green, nearest to RHS 146B. Venation — Type — Pinnate. Vein color, adaxial surface — Green, nearest to RHS 137B. Vein color, abaxial surface — Yellow-green, nearest to RHS N148B. Petiole — Length — 15.8 cm. Diameter — Petioles flattened; 0.3 wide and 0.25 cm tall. Strength — Moderately strong. Texture, adaxial and abaxial surfaces — Densely covered with soft hairs; average length of hairs is 0.1 cm; colored white, RHS 156D. Luster, adaxial and abaxial surfaces — Moderately glossy. Color, adaxial surface — Yellow-green, nearest to RHS 144B. Color, abaxial surface — Yellow-green, nearest to RHS 144B. Stipules — None present.

*Leaves borne on the stems*.—Quantity — Approximately 3 leaves per stem. Attachment — Petiolate. Division — Simple. Leaf shape — Trilobate; lobes are deeply lobed to near-cleft. Lobes — Depth of sinuses — Deep. Sinus orientation — Divergent. Dimensions — 3.7 cm long, excluding the petiole, and 3.6 cm wide. Leaf attitude — Leaves in an average angle of 50 degrees to the stem. Leaf apex — Narrow acute. Leaf base — Acuminate. Leaf margin — Coarsely serrate. Texture, adaxial and abaxial surfaces — Smooth, pubescent. Pubescence, adaxial and abaxial surfaces — Soft, appressed to strigose hairs with an average length of 0.1 cm; colored a translucent white, nearest to RHS N155A. Luster, adaxial surface — Matte. Luster, abaxial surface — Matte. Color — Juvenile foliage color, adaxial surface — Green, nearest to RHS 143B. Juvenile foliage color, abaxial surface — Yellow-green, nearest to RHS 146C. Mature leaf color, adaxial surface — Green, nearest to RHS 137B. Mature leaf color, abaxial surface — Yellow-green, nearest to RHS 146B. Venation — Type — Pinnate. Vein color, adaxial surface — Green, nearest to RHS 137B. Vein color, abaxial surface — Yellow-green, nearest to RHS N148B. Petiole — Length — 1.5 cm. Diameter — Petioles flattened; 0.3 wide and 0.25 cm tall. Strength — Moderately strong. Texture, adaxial and abaxial surfaces — Densely covered with soft hairs; average length of hairs is 0.1 cm; colored white, RHS 156D. Luster, adaxial and abaxial surfaces — Moderately glossy. Color, adaxial surface — Yellow-green, nearest to RHS 144B. Color, abaxial surface — Yellow-green, nearest to RHS 144B. Stipules — General — Two leafy stipules present at the base of each leaf. Shape — Ovate. Length — 1.8 cm. Diameter — 0.8 cm. Apex — Narrow acute. Base — Cuneate. Margins — Serrate. Texture, adaxial and abaxial surfaces — Densely covered with soft hairs; average length of hairs is 0.1 cm; colored white, RHS N155A. Luster, adaxial and abaxial surfaces — Moderately glossy. Color, adaxial surface — Yellow-green, nearest to RHS 144B. Color, abaxial surface — Yellow-green, nearest to RHS 144B.

Inflorescence:

*Habit.*—Compound cyme.

*Natural flowering season.*—Spring into summer in Kirkcudbright, Scotland.

*Time to flower or response time.*—Approximately 9 months.

*Dimensions.*—8.4 cm high, from lowest cauline petiole, and 10.5 cm in diameter.

*Quantity of inflorescence per plant.*—24, on average.

*Quantity of flowers per inflorescence.*—5, on average.

*Quantity of flower buds per plant.*—115, on average.

*Quantity of flowers and flower buds per plant.*—120, on average.

*Peduncles.*—Length — Average of 6.7 cm. Diameter — Average of 0.3 cm. Angle — Average angle to stem is 30 degrees. Strength — Moderately strong to strong. Texture — Smooth and densely pubescent; hairs are soft with an average length of 0.1 cm; colored white, nearest to RHS N155A. Luster — Moderately glossy. Color — Yellow-green, nearest to RHS 146B, with the upper side suffused in between purple and brown, RHS 187A and 200B.

Flower buds:

*Shape.*—Flattened deltoid.

*Length.*—0.7 cm.

*Diameter.*—0.8 cm.

*Texture.*—Smooth and moderately pubescent; hairs are soft with an average length of 0.1 cm; colored white, nearest to RHS N155A.

*Luster.*—Very slightly glossy.

*Color.*—Greyed-red, nearest to RHS 178A but slightly darker; base is yellow-green, nearest to RHS 145A.

Flower:

*Shape, type.*—Rotate; double.

*Flowering habit.*—Freely flowering.

*Aspect.*—Upright to outward.

*Flower longevity on plant.*—Approximately ten days.

*Persistent or self-cleaning.*—Self-cleaning.

*Fragrance.*—Non-fragrant.

*Diameter.*—5.9 cm.

*Depth.*—3.0 cm.

*Pedicels.*—Length — 4.7 cm. Diameter — 0.2 cm. Angle — Average angle to peduncle is approximately 35 degrees. Strength — Moderately strong. Texture — Smooth and densely pubescent; hairs are soft with an average length of 0.1 cm; colored white, nearest to RHS N155A. Luster — Slightly glossy. Color — Yellow-green, nearest to RHS 146B, with the upper side suffused in between purple and brown, RHS 187A and 200B.

*Calyx.*—Shape — Rotate. Length — 0.9 cm. Diameter — 1.5 cm. Sepals — Arrangement — Rotate; one whorl of sepals which alternate between broad sepals and narrow sepals. Quantity — 10 unfused sepals; 5 broad sepals and 5 narrow sepals. Broad sepals — Shape — Deltoid. Dimensions — 1.0 cm long and 0.8 cm wide. Apex — Acute. Base — Straight. Sepal reflex — Strongly reflexed. Margin — Entire. Texture and luster, upper surface — Smooth, glabrous, and very slightly glossy. Texture and luster, lower surface — Smooth, moderately covered with soft strigose hairs, and very slightly glossy; hairs are approximately 0.075 cm long and colored white, nearest to RHS N155A. Color — When opening, upper surface — Yellow-green, nearest to RHS 148B. When opening, lower surface — Brown, RHS 200D. Fully opened, upper surface — Yellow-green, nearest to RHS 147C; margins near the apex are very lightly suffused with greyed-orange, nearest to a mixture of RHS 177B, 177C and 177D. Fully opened, lower surface — Yellow-green, nearest to RHS 147B; veins and margins near the apex are very lightly suffused with greyed-orange, nearest to a mixture of RHS 177B, 177C and 177D. Narrow sepals — Shape — Narrow elliptic. Dimensions — 0.4 cm long and 0.15 cm wide. Apex — Acute. Base — Attenuate. Sepal reflex — Slightly reflexed. Margin — Entire. Texture and luster, upper surface — Smooth, glabrous, and very slightly glossy. Texture and luster, lower surface — Smooth, moderately covered with soft strigose hairs, and very slightly glossy; hairs are approximately 0.075 cm long and colored white, nearest to RHS N155A. Color — When opening, upper surface — Yellow-green, nearest to RHS 148B. When opening, lower surface — Brown, RHS 200D. Fully opened, upper surface — Yellow-green, nearest to RHS 147C; margins near the apex are very lightly suffused with greyed-orange, nearest to a mixture of RHS 177B, 177C and 177D. Fully opened, lower surface — Yellow-green, nearest to RHS 147B; veins and margins near the apex are very lightly suffused with greyed-orange, nearest to a mixture of RHS 177B, 177C and 177D.

*Petals*.—Quantity — 20, on average. Arrangement — Rotate; arranged in four whorls of unfused petals. Length — 2.1 cm. Width — 2.7 cm. Shape — Reniform. Apex — Broad emarginate. Base — Broad attenuate. Margin — Entire; highly undulate. Texture, upper surface — Glabrous, moderately velvety and matte. Texture, lower surface — Glabrous, very slightly rugose, and matte. Petal color — When opening, upper surface — Marbled with a combination of orange and orange-red, nearest to RHS 28A, N30A, N30B, 33A and 33B. When opening, lower surface — Orange, nearest to RHS 25C, and becoming orange-red towards the apex, nearest to RHS 31B. Fully opened, upper surface — Orange-red, nearest to RHS 32A, and fading darker towards the apex, nearest to RHS 34A. Fully opened, lower surface — Orange-red, nearest to RHS 31B, and becoming red towards the apex, nearest to RHS 35A. When faded, upper surface — Orange-red, nearest to RHS 34A. When faded, upper surface — Orange-red, nearest to RHS N34C. Petal venation color — Fully opened, upper surface — Red; nearest to RHS 42B. Fully opened, lower surface — Red; nearest to RHS 42B.

Reproductive organs:

*Androecium*.—Stamens — Quantity — Approximately 125. Anthers — Attachment — Dorsifixed. Shape — Oblong. Dimensions — 0.1 cm long and 0.03 cm wide. Color — Yellow-orange, nearest to RHS 22A. Filaments — Length — 0.6 cm. Color — Yellow, nearest to RHS 12A. Amount of Pollen — Sparse. Pollen color — Yellow, nearest to RHS 12A.

*Gynoecium*.—Pistil — Quantity — 50, on average. Length — 0.5 cm. Style — Length — 0.45 cm. Color — Orange, RHS 23B, and fading lighter towards the base, nearest to RHS 23C. Stigma — Shape — Cleft; two-parted. Length — 0.05 cm. Diameter — 0.05 cm. Color — Red, RHS 53A. Ovary Color — Green, RHS 138A.

Seed and fruit: No fruit or seeds have been detected to date.

Comparisons with the parent plants: Plants of the new cultivar 'MACGEU005' differ from its seed parent, *Geum* sp. 'Hannay's' (unpatented), by the characteristics described in Table 1.

TABLE 1

| Characteristic | 'MACGEU005' | 'Hannay's' |
|---|---|---|
| Plant vigor. | More vigorous than 'Hannay's'. | Less vigorous than 'MACGE005'. |
| General coloration of the flower. | Orange-red. | Orange. |
| Bloom period. | Longer than 'Hannay's'. | Shorter than 'MACGE005'. |

Plants of the new cultivar 'MACGEU005' may be distinguished from its pollen parent, *Geum chiloense* 'Red Dragon' (unpatented), by the characteristics described in Table 2.

TABLE 2

| Characteristic | 'MACGEU005' | 'Red Dragon' |
|---|---|---|
| Plant vigor. | More vigorous than 'Red Dragon'. | Less vigorous than 'MACGE005'. |
| Bloom period. | Longer than 'Red Dragon'. | Shorter than 'MACGE005'. |

Comparison with the most similar variety of common knowledge : Plants of the new cultivar 'MACGEU005' may be distinguished from the most similar known commercial comparator, *Geum* 'MACGEU001' (U.S. Plant Pat. No. 28,476), by the characteristics described in Table 3.

TABLE 3

| Characteristic | 'MACGEU005' | 'MACGEU001' |
|---|---|---|
| Foliage size. | Larger than 'MACGEU001'. | Smaller than 'MACGEU005'. |
| Abundance of flowers. | More abundant than 'MACGEU001'. | Less abundant than 'MACGEU005'. |
| Flower petal quantity. | More petals than 'MACGEU001'. | Fewer petals than 'MACGEU005'. |

That which is claimed is:

1. A new and distinct variety of *Geum* hybrid plant named 'MACGEU005', substantially as described and illustrated herein.

* * * * *